(12) United States Patent
Guo

(10) Patent No.: US 11,058,873 B2
(45) Date of Patent: Jul. 13, 2021

(54) INTRA-CARDIAC IMPLANT, CARDIAC PACEMAKER, IMPLANTATION DEVICE AND METHOD FOR IMPLANTING INTRA-CARDIAC IMPLANT

(71) Applicant: Chengjun Guo, Beijing (CN)

(72) Inventor: Chengjun Guo, Beijing (CN)

(73) Assignee: Chengjun Guo, Beijing (CN)

( * ) Notice: Subject to any disclaimer, the term of this patent is extended or adjusted under 35 U.S.C. 154(b) by 350 days.

(21) Appl. No.: 15/965,612

(22) Filed: Apr. 27, 2018

(65) Prior Publication Data

US 2019/0255318 A1 Aug. 22, 2019

(30) Foreign Application Priority Data

Feb. 16, 2018 (CN) .......................... 201810158832.4

(51) Int. Cl.
```
A61N 1/05      (2006.01)
A61N 1/375     (2006.01)
A61B 17/34     (2006.01)
A61N 1/362     (2006.01)
A61N 1/372     (2006.01)
```
(52) U.S. Cl.
CPC ........ *A61N 1/0573* (2013.01); *A61B 17/3468* (2013.01); *A61N 1/057* (2013.01); *A61N 1/362* (2013.01); *A61N 1/3756* (2013.01); *A61N 1/37205* (2013.01); *A61N 1/37288* (2013.01); *A61N 1/37512* (2017.08); *A61N 1/37518* (2017.08); *A61N 2001/058* (2013.01); *A61N 2001/0578* (2013.01)

(58) Field of Classification Search
CPC . A61N 1/3756; A61N 1/0573; A61N 1/37205
See application file for complete search history.

(56) References Cited

U.S. PATENT DOCUMENTS

| | | | |
|---|---|---|---|
| 2007/0135883 A1* | 6/2007 | Drasler ................ | A61B 5/6848 607/126 |
| 2008/0039904 A1* | 2/2008 | Bulkes ................. | A61N 1/3622 607/62 |
| 2016/0310722 A1* | 10/2016 | Demmer ............ | A61N 1/36592 |
| 2019/0083800 A1* | 3/2019 | Yang .................... | A61N 1/3756 |

FOREIGN PATENT DOCUMENTS

| CN | 104203341 | 12/2014 |
|---|---|---|
| CN | 107106849 | 8/2017 |
| CN | 107233665 | 10/2017 |

* cited by examiner

*Primary Examiner* — Joseph M Dietrich
(74) *Attorney, Agent, or Firm* — Treasure IP Group, LLC

(57) ABSTRACT

Disclosed is an intra-cardiac implant, a device and a method for respectively implanting two connected intra-cardiac implants to two cardiac chambers at one time. The intra-cardiac implant comprises a columnar housing including a sidewall, a first terminal and a second terminal, a first connecting portion located at the first terminal of the housing and configured to connect with the implantation device; and a hook body mounted at the sidewall of the housing and comprising a fixed end on the sidewall and a free end stretching from the fixed end, wherein the hook body is configured to form a clamping structure with the sidewall, the free end comprises a tip on its top for piercing the myocardium, and the intra-cardiac implant is clamped between the hook body and the sidewall, so that the intra-cardiac implant is fixed on the myocardium.

19 Claims, 6 Drawing Sheets

INTRA-CARDIAC IMPLANT, CARDIAC PACEMAKER, IMPLANTATION DEVICE AND METHOD FOR IMPLANTING INTRA-CARDIAC IMPLANT

CROSS-REFERENCE TO RELATED APPLICATION

This application claims the benefit of Chinese Patent Application No. 201810158832.4, filed on Feb. 26, 2018, which is incorporated herein by reference in its entirety.

BACKGROUND OF THE DISCLOSURE

Field of the Disclosure

The present disclosure relates to the field of implantable medical devices, and more particularly to an intra-cardiac implant, a micro leadless cardiac pacemaker, an implantation device and a method for implanting the two connected intra-cardiac implants.

Background

Placing a micro-implant into a cardiac chamber is a recent development for diagnosis and treatment in modern medicine. Intra-cardiac micro-implants include sensors configured to acquire parameters such as cardiac electrical activity, blood pressure, blood flow and blood biochemical indexes, and micro treatment equipment configured to perform treatments such as sustained drug release or cardiac pacing in the long term. To place a micro-implant into the cardiac chamber, an interventional catheterization should be performed to deliver the micro-implant to a specific location in the cardiac chamber and then fix it to avoid complications such as implant failure or embolism due to dislocation or dislodgment.

A cardiac pacemaker is a widely used human-body implant. Nowadays, millions of people around the world benefit from artificial cardiac pacemakers implanted for maintaining normal heartbeats. When implanting a cardiac pacemaker, physicians usually place the cardiac pacemaker under the thoracic muscle of patients and implant one or several leads and electrodes into the cardiac chamber to sense cardiac electrical activity and stimulate the beating of the myocardium. However, openings and closings of cardiac valves are impacted by the leads every time the heart beats, and complications including heart failure (HF) can be caused over time due to changes in cardiac hemodynamics. A newly developed micro leadless cardiac pacemaker with no need of leads is configured to have the same size and shape as a pharmaceutical capsule, and can be directly placed in the cardiac chamber without impacting the openings and closings of the cardiac valves. Therefore, the complications can be reduced and operations can be simplified. Due to the small volume of the leadless pacemaker, a brand new implantation experience is created for the patient and infection rates using the transvenous implant system are greatly reduced.

The procedure and the method to implant the micro leadless pacemaker at a predetermined location in the cardiac chamber is challenging. Due to the impact of heart contractions and blood flow, the micro leadless pacemaker may detach from the myocardium or shift and move around within the cardiac chamber. It turns out that development of a micro leadless pacemaker delivery tool for implanting two connected micro pacemakers in the ventricle and atrium to achieve dual chamber cardiac pacing is a big technical challenge.

A single-end attachment manner is adopted for the existing micro leadless pacemaker. Currently, a spiral metal wire or a hook is formed at one terminal of the housing of the micro leadless pacemaker for screwing into the myocardium or hooking the reticular myocardial structure in the cardiac chamber to achieve fixation. Due to the impact of heart contraction and blood flow, the micro leadless pacemaker may be detached from the myocardium, or shift and move around in the cardiac chamber, resulting in an embolism or a poor contact between the electrodes and the myocardium, which may affect sensing and pacing thresholds. Moreover, due to the lack of reticular myocardial structure in the atrium, the current fixation devices cannot achieve atrial pacing and dual-chamber cardiac pacing, and as a result, the pacing effect and safety cannot be guaranteed.

SUMMARY OF THE DISCLOSURE

In view of this, there is provided a laterally fixed intra-cardiac implant, which is delivered to the cardiac chamber by use of an implantation device, comprising:
 a columnar housing including a sidewall, a first terminal and a second terminal,
 a first connecting portion located at the first terminal of the housing and configured to connect with the implantation device; and
 a hook body mounted at the sidewall of the housing and comprising a fixed end on the sidewall and a free end stretching from the fixed end,
 wherein the hook body is configured to form a clamping structure with the sidewall, the free end comprises a tip on its top for piercing the myocardium, and the intra-cardiac implant is clamped between the hook body and the sidewall, so that the intra-cardiac implant is fixed on the myocardium.

Preferably, the fixed end of the hook body is adjacent to the first terminal and the free end of the hook body is configured to extend outward relative to an axis of the housing.

Preferably, the hook body has a barb wherein the barb is adjacent to the tip of the hook body.

Preferably, the second terminal comprises a groove for containing the barb on the hook body abutting the sidewall before the hook body pierces the myocardium.

Preferably, the hook body is made of rigid material or shape-memory metal and the barb is made of semi-soft material or shape-memory alloy.

Preferably, the intra-cardiac implant comprises at least one hook body and each hook body contains at least one barb.

Preferably, the housing is used for sealing batteries and logic circuits of a pulse generator. The intra-cardiac implant further comprises at least one electrode mounted on the sidewall. The pulse generator is powered by the batteries and connected to at least one electrode for generating electrical pulses, and the intra-cardiac implant is used as a pacemaker.

Preferably, at least one portion of the sidewall is flat and used for mounting at least one electrode.

Preferably, at least one electrode comprises an electrode tip exposed at a surface of the sidewall, and the electrode tip is spherical, hemispherical or cylindrical.

Preferably, at least one electrode is made of metallic conductor or composite conductor, and the composite conductor comprises metallic conductor and an anti-inflammatory drug.

Preferably, the housing is used for sealing batteries and sensors. The sensors are used for sensing at least one of cardiac electrical activity, blood pressure, blood flow and blood biochemistry, and the intra-cardiac implant is used as a device for monitoring at least one physiological parameter.

Preferably, the housing is configured to contain medicine and comprises a release hole for releasing the medicine, and the intra-cardiac implant is used as a device for supplying medicine.

Preferably, the first connecting portion has a cylindrical structure with external threads and is connectable to an operating rod.

Preferably, the second terminal comprises a second connecting portion, and the second connecting portion comprises threaded holes, wherein each of the threaded holes is matched with the external threads of the first connecting portion.

According to another aspect of the disclosure, there is provided a cardiac pacemaker, comprising:

two above-mentioned intra-cardiac implants, wherein the two intra-cardiac implants are interconnected with each other.

Preferably, the two intra-cardiac implants are connected to each other by connecting to a communication module through soft wires.

Preferably, the two intra-cardiac implants are placed in different cardiac chambers, for achieving dual-chamber cardiac pacing.

According to another aspect of the disclosure, there is provided an implantation device for implanting an intra-cardiac implant, comprising:

an operating rod for controlling actions of the intra-cardiac implant;

a catheter for communicating a predetermined location and an external space to provide a guide and travel path for the intra-cardiac implant; and a containing tube configured to protect channel tissue and inner walls of the catheter from being scratched by the intra-cardiac implant, and to recapture the intra-cardiac implant.

According to another aspect of the disclosure, there is provided a method for implanting an intra-cardiac implant, comprising:

connecting the first connecting portion of the intra-cardiac implant mentioned above, wherein the hook body of the intra-cardiac implant is in a contracted state and is contained in the implantation device;

delivering the intra-cardiac implant by use of the implantation device to a predetermined location in the cardiac chamber;

operating the implantation device to make the hook body pierce the myocardium; and rotating the implantation device to separate the implantation device from the intra-cardiac implant, wherein the free end of the hook body pierces the myocardium and clamps the myocardium with a side surface of the housing, so that the intra-cardiac implant is fixed on the myocardium.

Preferably, two the intra-cardiac implants being connected with each other are implanted into two respective cardiac chambers during one implantation procedure, and during the implantation procedure, the two intra-cardiac implants are connected through threads which have a different thread direction from the thread direction of the connecting threads of the implantation device, so that the two intra-cardiac implants can be released one by one.

The implantation device according to the disclosure adopts an attachment method combined with clamping and hooking, so that the intra-cardiac implant is better fixed on the myocardium and the contact between the electrode and the myocardium is firmer. The method for fixing the intra-cardiac implant is safe and reliable, which can avoid the shift and the movement of the intra-cardiac implant due to the impact of heart contraction and blood flow, and therefore, the reliability, safety and practicability of the intra-cardiac micro implant are improved. This disclosure provides the device and method, which can implant two connected implants into two cardiac chambers at one time, so that leadless dual-chamber cardiac pacing is achieved without the need for Bluetooth communication technology.

BRIEF DESCRIPTION OF THE DRAWINGS

The above and other objects, advantages and features of the present invention will become more fully understandable from the detailed description given hereinbelow in connection with the appended drawings, and wherein.

DETAILED DESCRIPTION OF THE DISCLOSURE

Figure 1:
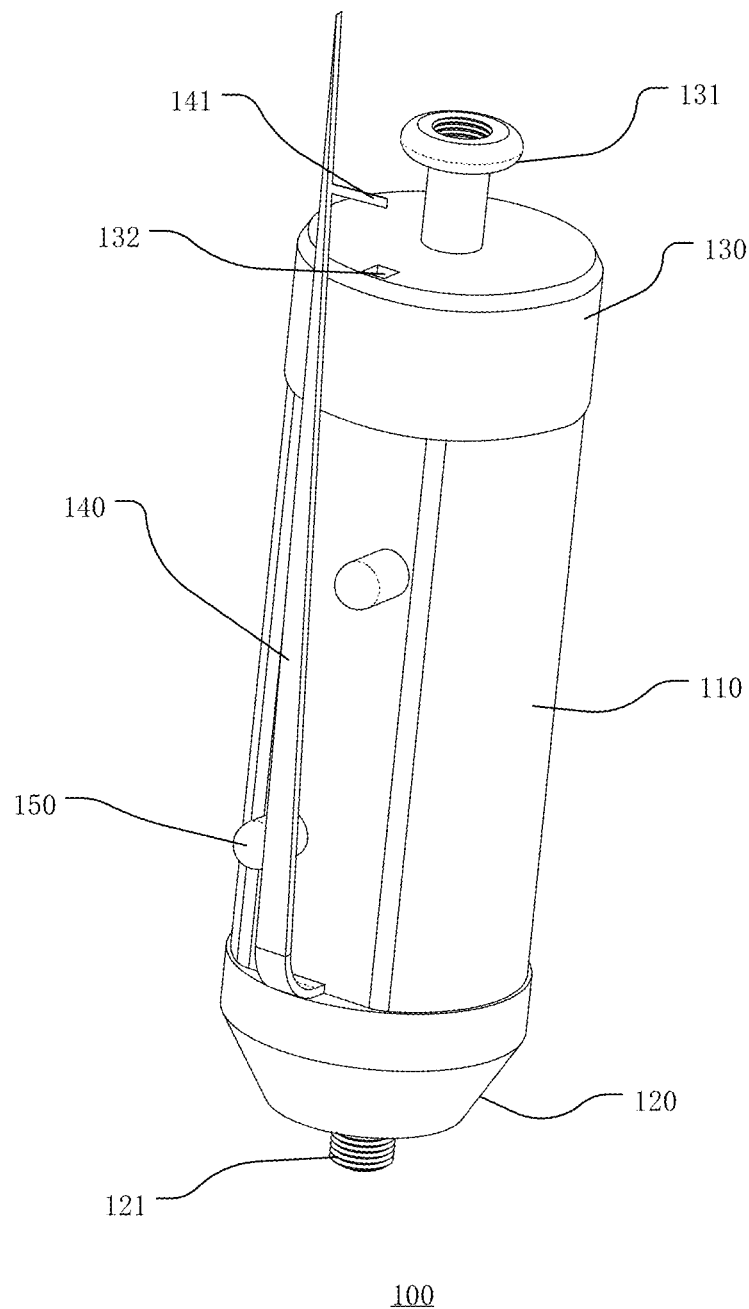
FIG. 1 is a structural diagram of an intra-cardiac implant according to a first embodiment of the disclosure.

Exemplary embodiments of the present disclosure will be described in more details below with reference to the accompanying drawings. In the drawings, like reference numerals denote like members. The figures are not drawn to scale, for the sake of clarity.

In the following description, a pacemaker is used as an example to describe an intra-cardiac implant. However, it should be understood that the intra-cardiac implant according to the disclosure is not limited to a pacemaker, but may be any one selected from a pacemaker, a monitoring device for monitoring physiological parameters, and a supply device for supplying medicine.

FIG. 1 is a structural diagram of an intra-cardiac implant 100 according to a first embodiment of the disclosure. The intra-cardiac implant 100 includes a housing 110, a first terminal 120 on the bottom of the housing, a second terminal 130 on the top of the housing, a hook body 140 mounted on the sidewall of the housing, and two electrodes 150 mounted on the sidewall of the housing.

The housing 110 is columnar, for example, cylindrical. The material of housing 101 is, for example, any one selected from plastics, ceramics and metallic materials. Further, the housing 110 includes a sidewall and two terminals. One portion of the sidewall is flat and used for mounting the hook body 140 and the electrodes 150. The first terminal is provided on the bottom of the housing 110, the first terminal 120 has a first connecting portion 121, the first connecting portion 121 is a cylindrical structure with external threads extending outward along the axis of the intra-cardiac implant 100 and can be connected to an operating rod. The second terminal 130 is provided on the top of the housing 110, the second terminal 130 has a second connecting portion 131, the second connecting portion 131 is a rod-shaped structure with a flange on the top. The flange has threaded holes at its center and the threaded holes match the external threads of the first connecting portion 121. The electrode 104 extends through the opening in the housing 101 from the interior of the housing 104 to the exterior of the housing 104, forming an electrode tip. The shape of the electrode tip of the electrode 104 is selected from one of sphere, hemisphere and cylinder. The electrode 104 is made of metallic conductor or composite conductor which includes metallic conductor and an anti-inflammatory drug. The housing 101 is electrically isolated from the electrode 104. Accordingly, at least the portion of the housing 101 in contact with the electrode 104 is made of insulating material, or an insulation layer is adopted to isolate the housing 101 from the electrode 104.

The internal space of the housing 110 is used for sealing batteries and a pulse generator. The pulse generator is connected to the batteries to obtain electrical energy and is connected to the electrode 150 to provide electrical pulses based on a sensing signal or an external signal. Alternatively, the internal space of the housing 110 further includes a signal processing module and a communication module. The signal processing module is configured to obtain the sensing signal according to the signals from the sensor, and the communication module is configured to receive the external signal.

The hook body 140 is located on the sidewall of the housing 110. The hook body 140 includes a fixed end on the sidewall and a free end extending from the fixed end. The fixed end of the hook body 140 is mounted on the sidewall of the housing 110 in one of the following ways: socketing, welding or gluing. The hook body 140 is made of, for example, a rigid material or a shape-memory alloy. In the embodiment shown by FIG. 1, the fixed end of the hook body 140 is adjacent to the first terminal 120, and the free end of the hook body extends relative to the axis of the housing outwards slightly. The hook body 140 and the housing 110 form a clamping structure similar to a cap of pen. The free end has a tip on its top, for piercing the myocardium. The free end also has a barb 141 extending obliquely downward and located close to the top of the side surface of the free end, in order to achieve reverse hooking, and thus preventing backward movement. Two electrodes 150 are located on two sides of the hook body 140, being offset with each other along the axial direction of the housing 110.

During the implantation process, when the implant has not reached the predetermined location, the hook body 140 is pressed in the radial direction, the hook body 140 is close to the sidewall of the housing 110, the obliquely downward barb 141 is interfered with the second terminal 130. Therefore, a groove 132 is provided on a corresponding location on the second terminal for containing the pressed barb 141 on the hook body 140.

Due to the adoption of the fixation method combined by clamping and hooking similar to a cap of a pen, the intra-cardiac implant 100 according to the embodiment may include any number of hook bodies 140 and any number of electrodes 150, at any location on the sidewall to achieve multi-point fixation and/or multi-point pacing stimulation.

Figure 2:
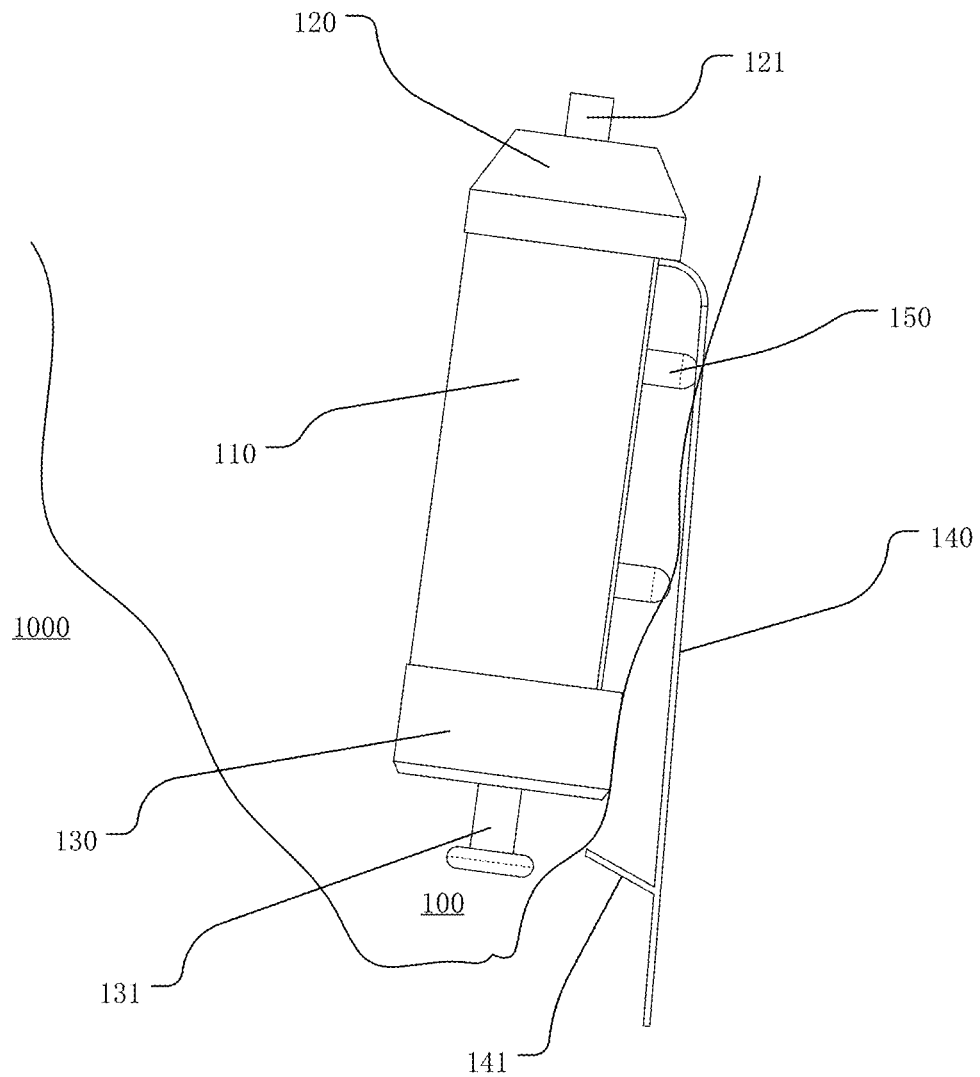
FIG. 2 is a structural diagram of an intra-cardiac implant after being implanted according to the first embodiment of the disclosure.

FIG. 2 is a structural diagram of an intra-cardiac implant after being implanted according to the first embodiment of the disclosure. The intra-cardiac implant 100 includes the housing 110, the first terminal 120 on one side of the housing, the second terminal 130 on the other side of the housing, the hook body 140 mounted on the sidewall of the housing, and two electrodes 150 mounted on the sidewall of the housing.

The hook body 140 is located on the sidewall of the housing 110. The hook body 140 includes the fixed end on the sidewall and the free end extending from the fixed end. The fixed end of the hook body 140 is mounted on the sidewall of the housing 110 in one of the following ways: socketing, welding or gluing. The hook body 140 is made of, for example, rigid material or semi-soft material or shape-memory alloy. The fixed end of the hook body 140 is adjacent to the first terminal 120, the free end of the hook body extends relative to the axis of the housing and stretches outward slightly. The hook body 140 uses the tip on its top to pierce the myocardium and is partially inserted into the myocardium. The free end also has a barb 141 extending obliquely downward and located close to the top of the side surface of the free end, in order to achieve hooking after piercing into the myocardium. The two electrodes 150 are located at two sides of the hook body 140 on the sidewall of the housing, being offset with each other along the axial direction of the housing 110.

As shown in FIG. 2, the hook body 140 forms a clamping structure with the housing 110, the clamping structure is similar to a cap of a pen, so that the intra-cardiac implant 100 is in close contact with the myocardium 1000. The barb 141 of the hook body 140 hooks into the myocardium after the book body 140 pierces the myocardium, to prevent the intra-cardiac implant 100 from detaching from the myocardium 1000. Due to the adoption of the fixation method combined with clamping and hooking, the intra-cardiac implant 100 is more securely fixed on the myocardium and the contact between the electrode and the myocardium is firmer.

Preferably, the barb 141 of the hook body 140 is made of shape-memory alloy, for example. In the embodiment shown in FIG. 2, the barb 141 is located at the free end of the hook body 140. In a predetermined shape, the barb 141 stretches outwards and forms an acute angle with the body of the hook body 104. The predetermined shape is a shape pre-formed when the temperature is close to body temperature.

The intra-cardiac implant 100 according to this embodiment includes a hook body mounted on a sidewall of the housing. The tip on the top of the hook body pierces the myocardium, forming a clamping structure similar to a cap of pen, so that the intra-cardiac implant 100 is in close contact with the myocardium 1000. Then the barb 141 of the hook body 140 reversely hooks the myocardium after the hook body pierces the myocardium, so that the intra-cardiac implant 100 is fixed on the myocardium. The fixation method for fixing the intra-cardiac implant 100 is simple and practical. The fixation method combined with clamping and hooking adopted to fix the intra-cardiac implant 100 is safe and reliable. The hook body on the housing includes the barb. Due to the body's temperature, the barb stretches outwards after the hook body pierces the myocardium, and further the barb is used to hook the myocardium. The barb on the hook body can prevent the intra-cardiac implant 100 from shifting and moving due to heartbeats and blood flow, so that the reliability, safety and practicability of the intra-cardiac micro-implant are improved.

Figure 3:
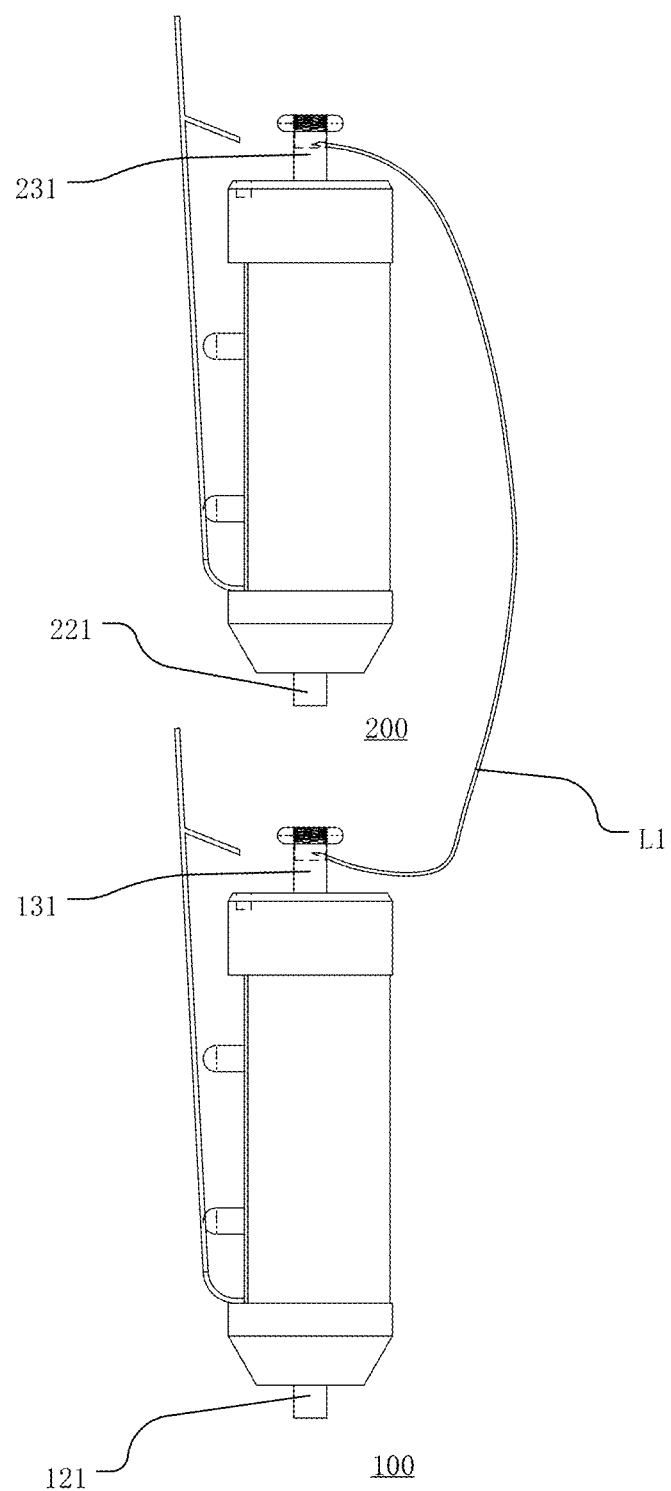
FIG. 3 is a structural diagram of an intra-cardiac implant according to a second embodiment of the disclosure.

FIG. 3 is a structural diagram of an intra-cardiac implant according to the second embodiment of the disclosure. In the second embodiment, two intra-cardiac implants as shown in FIG. 1 form a group of implants, being denoted as 100 and 200. The same portions are not repeatedly described here. The intra-cardiac implants 100 and 200 are connected with a lead L1, one end of the lead L1 is connected with the second connecting portion 131 of the intra-cardiac implant 100 and the other end is connected with the second connecting portion 231. The intra-cardiac implants 100 and 200 being connected with each other can be placed in the cardiac chamber and atria, and the lead L1 passes through the gap of the heart valve, thus achieving dual-chamber cardiac pacing. Certainly, the intra-cardiac implants 100 and 200 also can achieve interconnection by use of wireless communication modules in the implants instead of the lead L1. The disclosure provides the device and method, which can implant two connected implants into two cardiac chambers at one time, so that leadless dual-chamber cardiac pacing is achieved without the need for Bluetooth communication technology.

During implantation process, the second connecting portion 131 of the intra-cardiac plant 100 has threads matching with the external threads of the first connecting portion 221 of the intra-cardiac implant 200, and after the front intra-cardiac implant 200 is fixed, the intra-cardiac implant 100 is rotated to detach from the intra-cardiac implant 200. Preferably, the first connecting portion 221 and the second connecting portion 121 have opposite thread directions, so that the operating rod can be rotated in a different direction, to respectively release the intra-cardiac implants 100 and 200. For example, the front intra-cardiac implant 200 is released by rotating the operating rod in clockwise direction after it is fixed, and then the intra-cardiac implant 100 is released by rotating the operating rod in counterclockwise direction, and thus the intra-cardiac implants are fixed and released one by one.

Figure 4:
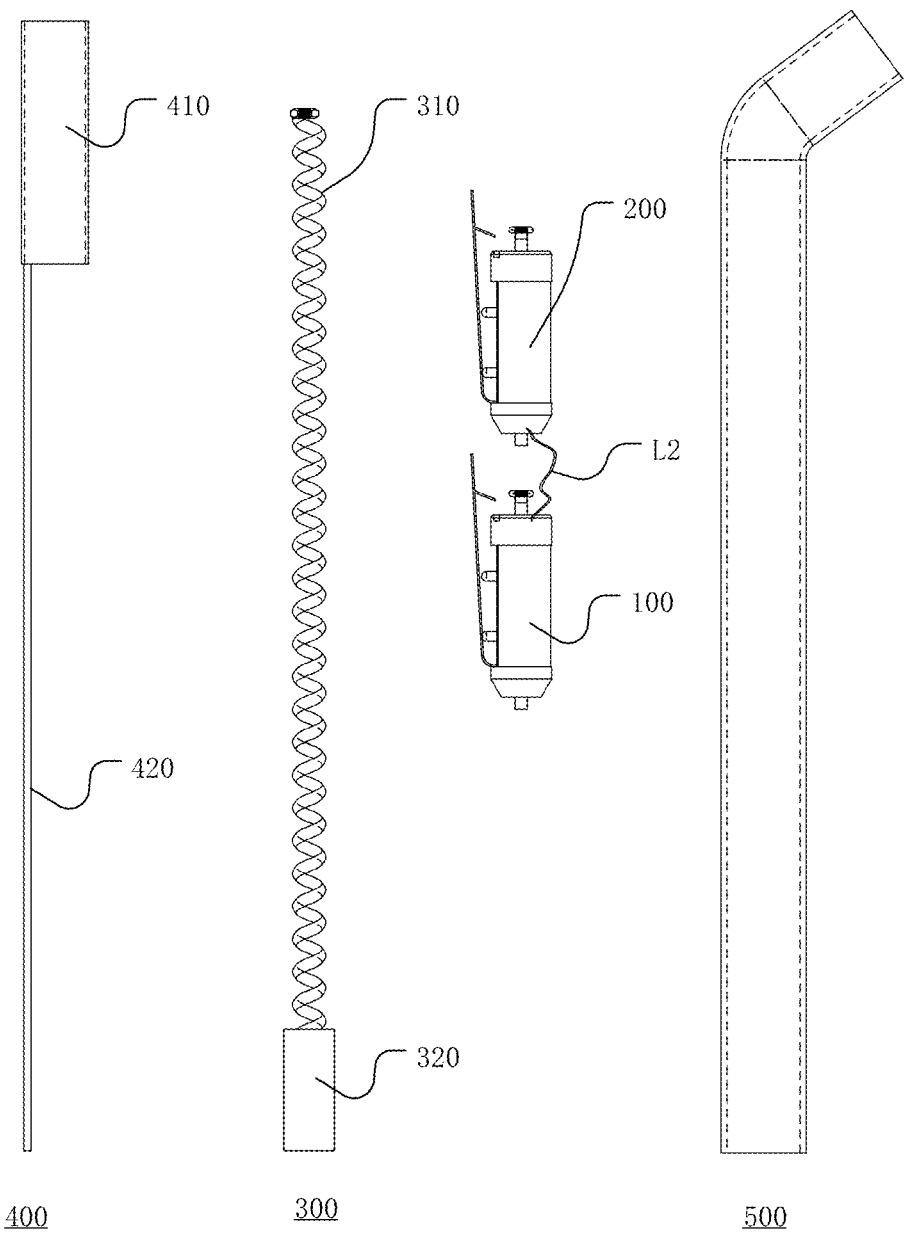
FIG. 4 is a structural diagram of an implantation device according to the second embodiment of the disclosure.
Figure 5:
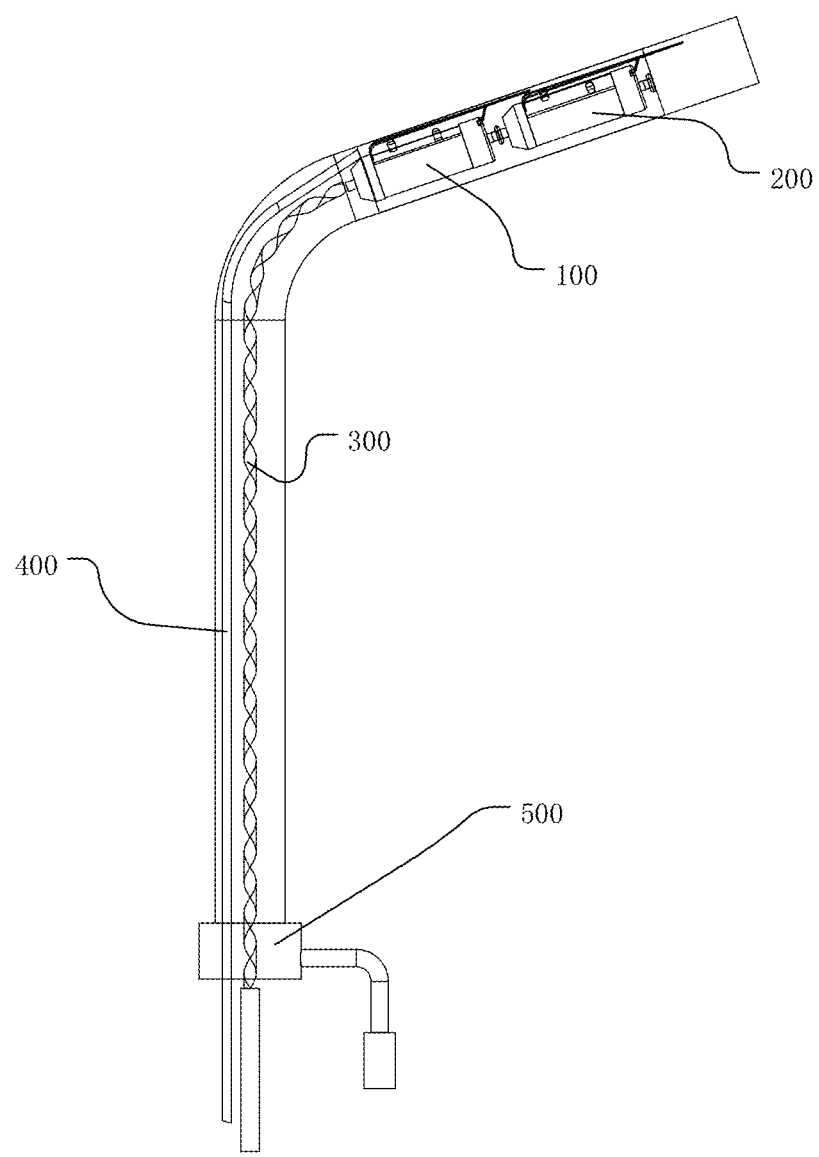
FIG. 5 is a structural diagram that shows the connection of the intra-cardiac implant with the implantation device in a delivery state according to the second embodiment of the present disclosure.

FIG. 4 is a structural diagram of an intra-cardiac implant and an implantation device according to the second embodiment. FIG. 5 is a structural diagram showing the connection of the intra-cardiac implant with the implantation device in a delivery state according to the second embodiment of the present disclosure. The intra-cardiac implants 100 and 200 shown in FIG. 4 also can be connected by a lead L2, of which one end is at the second terminal of the intra-cardiac implant 100, and the other end is at the first terminal of the intra-cardiac implant 200. Compared to the lead L1 shown in FIG. 3, the lead L2 has a shorter length, and thus it uses less material. In connection with FIG. 4 and FIG. 5, the implantation device according to the second embodiment is described below.

The implantation device includes an operating rod 300, a containing tube 400 and a catheter 500. The operating rod 300 includes a connecting rod 310 the top of which has a nut or a threaded hole structure corresponding to the external threads of the first connecting portion, and a connecting rod 310 has a shape that is elastically deformable. The containing tube 400 includes a sleeve 410 and a guide rod 420. The operating rod 300 has a diameter smaller than that of the implant, the sleeve 410 has a diameter slightly greater than that of the implant, and the catheter 500 has a diameter greater than that of the sleeve 410.

After the intra-cardiac implants 200 and 100 are combined, the top of the operating rod 300 is connected with the first connecting portion of the intra-cardiac implant 100, and then the combined intra-cardiac implants 200 and 100 are placed in the sleeve 410 of the containing tube 400. The hook body 140 is pressed in a radial direction so that it is close to the sidewall of the housing, and then the combined device is inserted into the catheter 500 The intra-cardiac implants can reach the predetermined location and complete the fixation, and can be released by controlling the operating rod 300 and the containing tube 400 through the catheter 500.

When the above intra-cardiac implants are installed into the cardiac chamber, minimally invasive surgery is performed to form an opening to a blood vessel. Next the operating rod 300, the containing tube 400 and the intra-cardiac implants are combined together, the catheter 500 is inserted into the opening and then is delivered to the predetermined location of the cardiac chamber along the blood vessel. Next the intra-cardiac implants are pushed by use of the operating rod 300 and the containing tube 400, so that the hook body of the intra-cardiac implant 200 pierces and hooks the myocardium along the axial direction of the housing, which makes the intra-cardiac implant 200 being fixed at the predetermined location of the cardiac chamber. Next the operating rod 300 is rotated in one direction to drive the intra-cardiac implants 100 and 200 to rotate relatively, so that the intra-cardiac implant 200 is released and separated. Next the fixation of the intra-cardiac implant 100 is performed, that is, similarly, the intra-cardiac implant 100 is pushed by use of the operating rod 300 and the containing tube 400, so that the hook body of the intra-cardiac implant 100 pierces and hooks the myocardium along the axial direction of the housing, which makes the intra-cardiac implant 100 fixed at the predetermined location in the cardiac chamber. Next the operating rod 300 is rotated in a reverse direction to the previous, so that the intra-cardiac implant 100 is detached from the operating rod 300. Finally, the operating rod 300, the containing tube 400 and the catheter 500 are withdrawn along the blood vessel, and the operating wound is sutured. The containing tube 400 is used to protect the channel tissue from being scratched by the implantation device after the device moves out of the catheter 500, also to protect the inner wall of the catheter from being damaged by the implant, and to reuse the implant during implantation. In the above delivery state, the operating rod 300 is rotated in two different directions, so that the intra-cardiac implants 100 and 200 are released one by one.

Figure 6:
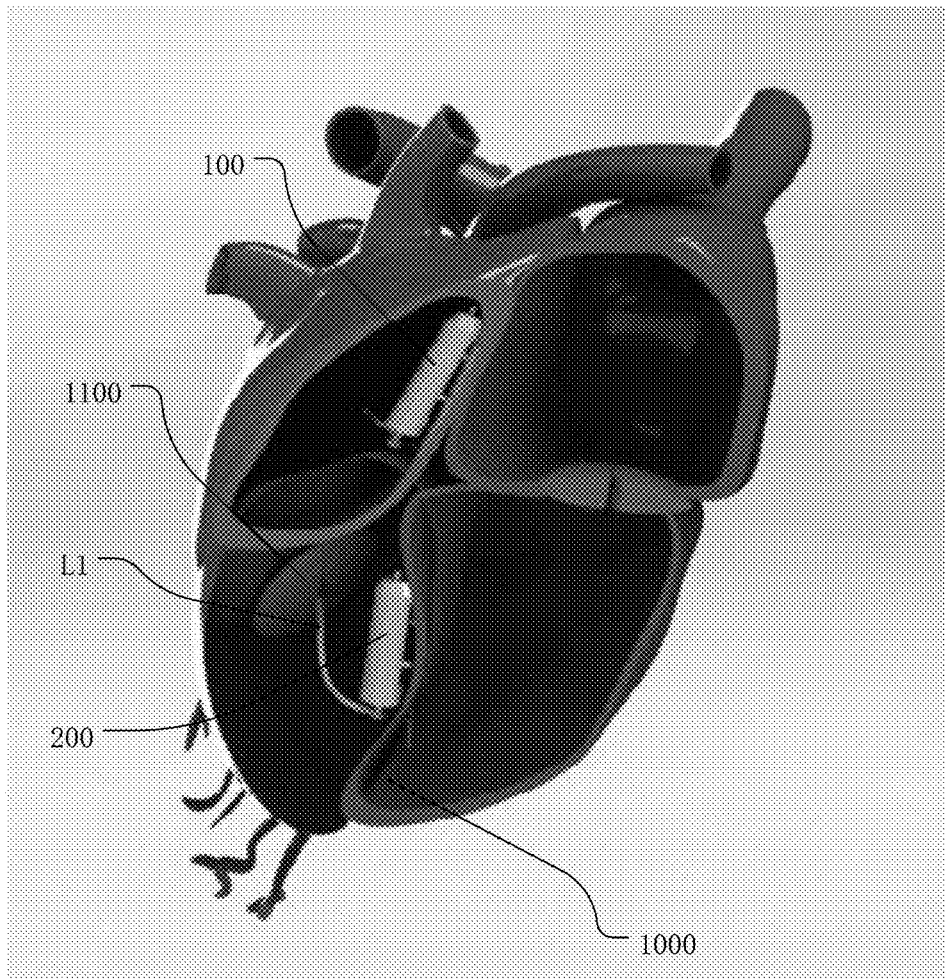
FIG. 6 is a structural diagram of an intra-cardiac implant after being fixed according to the second embodiment of the disclosure.

FIG. 6 is a structural diagram of an intra-cardiac implant after being fixed according to the second embodiment of the disclosure. As shown in FIG. 6, there are two respective intra-cardiac implants in the right cardiac chamber and right atrial of the heart. The two intra-cardiac implants are connected by the lead L1 to form a group of implants in the second embodiment. The lead L1 passes through the tricuspid valve 1100 of the heart to connect the intra-cardiac implant 100 with the intra-cardiac implant 200, the intra-cardiac implants 100 and 200 themselves are in contact with the myocardium of the heart, the free end of the hook body pierces the reticular myocardial structure of the heart, the hook body forms a clamping structure similar to a cap of pen with the housing, so that the intra-cardiac implant is in close contact with the myocardium 1000, and the barb of the hook body hooks the myocardium after the hook body pierces the myocardium. When the intra-cardiac implant is installed at the predetermined location in the heart chamber, the barb is restored to a predetermined shape due to the temperature of the human body. The barb stretches outwards and forms an acute angle with the body of the hook body, so that the intra-cardiac implant is fixed on the myocardium.

The embodiment adopts a fixation method for fixing the intra-cardiac implant combined with clamping and hooking, and the fixation method is safe and reliable. The hook body and housing form the clamping structure similar to the cap of a pen, so that the intra-cardiac implant is in close contact with the myocardium which make the electrodes and the myocardium contact well. The barb of the hook body can prevent the intra-cardiac implant from shifting and moving due to heartbeats and blood flow, which improves the reliability, safety and practicality of the intra-cardiac implant. The disclosure provides the device and method, which can implant two connected implants into two cardiac chambers at one time, so that wireless dual-chamber cardiac pacing is achieved without the need for Bluetooth communication technology.

The above embodiment describes the intra-cardiac implant serving as a pacemaker. The batteries and generator are contained inside the housing and are connected to a plurality of electrodes on the sidewall of the housing to achieve multi-point sensing and/or multi-point pacing. However, the present disclosure is not limited thereto. In an alternative embodiment, the intra-cardiac implant may be a physiological parameter monitoring device wherein the inside of the housing contains sealed batteries and sensors for sensing at least one of electrocardiogram, blood pressure, blood flow, and blood biochemicals. In another alternative embodiment, the intra-cardiac implant may be a drug delivery device wherein the housing contains a medication, including a release orifice for releasing the medication so that the medicament can be minutely supplied for a prolonged period of time.

In accordance with the embodiments of the present disclosure, as described above, these embodiments are not exhaustive of all the details and do not limit the disclosure to the specific embodiments described. Obviously, many modifications and variations are possible in light of the above description. The embodiments were chosen and described in order to best explain the principles of the invention and the practical application so that those skilled in the art may, without departing from the spirit and scope of the invention, utilize the invention and adapt it. Therefore, if these changes and modifications of the present invention fall within the scope of the claims of the present invention and its equivalent technologies, the present invention also intends to include these changes and modifications.

The invention claimed is:

1. An intra-cardiac implant, configured to be delivered into a cardiac chamber by use of an implantation device, comprising:
   a columnar housing including a sidewall, a first terminal and a second terminal;
   a first connecting portion, located at said first terminal of said columnar housing and configured to connect, to said implantation device; and
   a singular hook body, mounted at said sidewall of said housing and comprising a fixed end on said sidewall and a free end stretching from said fixed end;
   wherein said hook body is configured to form a clamping structure with said sidewall;
   said free end comprises a tip on its top for piercing the myocardium, and
   and the clamping structure capable of clamping and sandwiching the myocardium between a side surface of said housing and said hook body,
   so that said intra-cardiac implant is fixed on a myocardium,
   said second terminal comprises a groove, for accommodating a barb of said hook body abutment against the sidewall before the hook body pierces the myocardium.

2. The intra-cardiac implant according to claim 1, wherein said fixed end of said hook body is adjacent to said first terminal and said free end of said hook body extends outwardly in parallel to a longitudinal direction of said housing and is open to the outside to form an umbrella shape.

3. The intra-cardiac implant according to claim 1, wherein the barb is formed on said hook body, and said barb is adjacent to a tip of said hook body.

4. The intra-cardiac implant according to claim 3, wherein said hook body is made of a rigid material or a shape-memory metal, and said barb is made of a semi-soft material or shape-memory alloy.

5. The intra-cardiac implant according to claim 1, wherein said intra-cardiac implant comprises at least one hook body and each of the hook bodies comprises at least one barb.

6. The intra-cardiac implant according to claim 1, wherein said intra-cardiac implant further comprises
   batteries, sealed in said housing;
   at least one electrode, mounted on said sidewall;
   a pulse generator, being powered by said batteries and connected to said at least one electrode for generating electrical pulses,
   logic circuits of the pulse generator, sealed in said housing;
   and
   wherein said intra-cardiac implant is used as a pacemaker.

7. The intra-cardiac implant according to claim 6, wherein at least one portion of said sidewall is flat and used for mounting said at least one electrode.

8. The intra-cardiac implant according to claim 6, wherein said at least one electrode comprises an electrode tip exposed at a surface of said sidewall, and said electrode tip is spherical, hemispherical or cylindrical.

9. The intra-cardiac implant according to claim 6, wherein said at least one electrode is made of a metallic conductor or composite conductor, and said composite conductor comprises a metallic conductor and an anti-inflammatory drug.

10. The intra-cardiac implant according to claim 1, further comprising
    batteries, sealed inside the housing;
    and sensors, sealed inside the housing, configured to sense at least one of cardiac electrical activity, blood pressure, blood flow and blood biochemistry,
    wherein said intra-cardiac implant is used as a device for monitoring at least one physiological parameter.

11. The intra-cardiac implant according to claim 1, wherein said housing is configured to contain a drug and comprises a release hole for drug release, and said intra-cardiac implant is used as a device for drug supply.

12. The intra-cardiac implant according to claim 1, wherein said first connecting portion is a cylindrical structure with external threads and is connectable to an operating rod.

13. The intra-cardiac implant according to claim 12, wherein said second terminal comprises a second connecting portion, and said second connecting portion comprises threaded holes, each of said threaded holes can be matched with said external threads of said first connecting portion.

14. A cardiac pacemaker, comprising:
    two intra-cardiac implants according to claim 13,
    wherein said two intra-cardiac implants are interconnected with each other.

15. The cardiac pacemaker according to claim 14, wherein said two intra-cardiac implants are connected to each other by connecting to a communication module through soft wires.

16. The cardiac pacemaker according to claim 15, wherein said two intra-cardiac implants are placed in different cardiac chambers, for achieving dual-chamber cardiac pacing.

17. The cardiac pacemaker according to claim 1, wherein said cardiac pacemaker is comprised of
the intra-cardiac implant of claim 1 and
an implantation device,
said intra-cardiac implant is configured to be delivered to a target location through the implantation device,
the implantation device comprising:
an operating rod, configured to control actions of said intra-cardiac implant;
a catheter, configured to communicate a predetermined location and an external space information to provide a guide and travel path for said intra-cardiac implant; and
a containing tube, configured to protect channel tissue and inner walls of said catheter from being scratched by said intra-cardiac implant, and to recapture said intra-cardiac implant.

18. A method for implanting an intra-cardiac implant, comprising:
providing said intra-cardiac implant of claim 1;
connecting said first connecting portion of said intra-cardiac implant with the implantation device, wherein said hook body of said intra-cardiac implant is at a contracted state and is contained in said implantation device;
delivering said intra-cardiac implant by use of said implantation device to a predetermined location in the cardiac chamber;
operating said implantation device to make said hook body pierce the myocardium; and
rotating said implantation device to separate said implantation device from said intra-cardiac implant,
wherein said free end of said hook body pierces the myocardium, and clamps the myocardium with a side surface of said housing, so that said intra-cardiac implant is fixed on the myocardium.

19. The method according to claim 18, wherein two said intra-cardiac implants being connected with each other are implanted into two respective cardiac chambers during one implantation procedure, and during the implantation procedure, said two intra-cardiac implants are connected through threads which have a different thread direction from a thread direction of connecting threads of said implantation device, so that said two intra-cardiac implants can be released one by one.

* * * * *